United States Patent
Liu et al.

(10) Patent No.: US 11,753,688 B2
(45) Date of Patent: Sep. 12, 2023

(54) BIOMARKER FOR EARLY DIAGNOSIS AND PREOPERATIVE ASSESSMENT OF PHEOCHROMOCYTOMA/PARAGANGLIOMA, AND APPLICATION THEREOF

(71) Applicant: THE FIRST AFFILIATED HOSPITAL OF DALIAN MEDICAL UNIVERSITY, Liaoning (CN)

(72) Inventors: Jing Liu, Liaoning (CN); Liang Wang, Liaoning (CN); Jingyun Ma, Liaoning (CN)

(73) Assignee: THE FIRST AFFILIATED HOSPITAL OF DALIAN MEDICAL UNIVERSITY, Liaoning (CN)

( * ) Notice: Subject to any disclaimer, the term of this patent is extended or adjusted under 35 U.S.C. 154(b) by 237 days.

(21) Appl. No.: 17/251,651

(22) PCT Filed: Jun. 25, 2018

(86) PCT No.: PCT/CN2018/092624
§ 371 (c)(1),
(2) Date: Dec. 11, 2020

(87) PCT Pub. No.: WO2019/237425
PCT Pub. Date: Dec. 19, 2019

(65) Prior Publication Data
US 2021/0277484 A1 Sep. 9, 2021

(30) Foreign Application Priority Data
Jun. 14, 2018 (CN) .......................... 201810610358.4

(51) Int. Cl.
*C12Q 1/6886* (2018.01)
(52) U.S. Cl.
CPC ..... *C12Q 1/6886* (2013.01); *C12Q 2600/156* (2013.01)
(58) Field of Classification Search
None
See application file for complete search history.

(56) References Cited

U.S. PATENT DOCUMENTS

| | | | | |
|---|---|---|---|---|
| 2008/0139801 | A1* | 6/2008 | Umansky | C12Q 1/6806 536/25.41 |
| 2010/0196426 | A1* | 8/2010 | Skog | C12Q 1/6886 604/7 |
| 2013/0143275 | A1* | 6/2013 | Pasloske | C12N 15/1096 435/91.51 |
| 2017/0175200 | A1* | 6/2017 | Lyden | C12Q 1/6886 |

FOREIGN PATENT DOCUMENTS

CN 107893101 A 4/2018

OTHER PUBLICATIONS

Takahashi et al Nature Communications. May 16, 2017. 8:15287, p. 1-16 (Year: 2017).*
Peinado et al Nature Medicine. 2012. 18:883-891 and Online Methods, 13 pages total (Year: 2012).*
Kahlert et al. J Biol Chem. 2014. 289(7): 3869-3875 (Year: 2014).*
Hill etal J Extracellular Vesicles. 2013. 2: 22859, p. 1-8 (Year: 2013).*
Bayley et al BMC Medical Genetics. 2006. 7:1, p. 1-10 (Year: 2006).*
Zhao, An et al.; Tumor Exosomes: Diagnosis and Treatment; ID,010V, China Cancer, vol. 26, No. 3, Mar. 2, 2017, pp. 190-195.
Gong, Chunmei et al.; Advances in Research on Methods of Separation and Identification of Exosomes; Scientia Sinica(Vitae); vol. 30, No. 3, Mar. 31, 2017, pp. 319-326.

* cited by examiner

*Primary Examiner* — Carla J Myers
(74) *Attorney, Agent, or Firm* — NKL Law; Allen Xue (57) ABSTRACT

A double-stranded DNA biomarker derived from exosomes is useful in early diagnosis and preoperative evaluation of pheochromocytoma and paraganglioma, and applications thereof. The biomarker is genome double-stranded DNA fragment specifically derived from exosomes in blood serum of pheochromocytoma and paraganglioma patients. The double-stranded DNA can represent variations of RET, VHL, and HIF2A with high frequency of somatic cell mutation, and metastatic phenotype-related SDHB, which are susceptibility genes of PCCs and PGLs. The circulating exosome DNA in patient's peripheral blood contains 97% of the same chromosomal point mutation information as the tumor cells from which the DNA originated. There is evidence of the existence of double-stranded DNA in the serum exosomes of PCCs and PGLs. The double-stranded DNA can be used to identify mutations in tumor cells and provide a noninvasive molecular marker for the clinical diagnosis and preoperative evaluation of PCCs and PGLs.

7 Claims, 11 Drawing Sheets

B PC12 genomic DNA

Fig. 6 Continued a patient 1

Fig. 8

BIOMARKER FOR EARLY DIAGNOSIS AND PREOPERATIVE ASSESSMENT OF PHEOCHROMOCYTOMA/PARAGANGLIOMA, AND APPLICATION THEREOF

FIELD OF TECHNOLOGY

The present invention belongs to the field of tumor diagnosis and treatment, and specifically relates to a double-stranded DNA biomarker derived from exosomes for the early diagnosis and preoperative assessment of pheochromocytoma and paraganglioma.

BACKGROUND ART

Pheochromocytomas (PCCs) and paragangliomas (PGLs) are rare endocrine tumors that arise from adrenal medullary pheochromocyte. Approximately 50-80% of PCCs and PGLs are related to germline or somatic mutations of at least 12 genes of NF1, RET, VHL, SDHA, SDHB, SDHC, SDHD, SDHAF2, TMEM127, MAX, HIF2A, and FH. Furthermore, accompanied by the continuous accumulation of mutation detection data, recent genetic studies have identified 21 additional genes that are involved in PCC and PGL tumorigenesis. Compared with other tumors, PCCs and PGLs are characterized by remarkable genetic determinism. Specific genotype-phenotype correlations have been established between susceptibility gene mutations and their clinical presentations. Among the 12 susceptibility genes, the most frequently mutated genes are NF1, VHL, HIF2A, RET, and SDHB. SDHB mutations are associated with 40%-60% of metastatic PCCs and PGLs. Similarly, other susceptibility gene mutations also exhibit specific genotype-phenotype correlations. The assessment of germline mutations in 12 susceptibility genes is recommended for clinical diagnosis of all PCC and PGL patients who are with high risk of familial genetic history, syndromes, multiple tumors, malignant tumors, or a combination of some of these characteristics.

Susceptibility gene mutations should be evaluated for PCC and PGL patients before surgery: i) optimizing the surgery program, reducing the risk of operation and improving the survival rate; ii) providing personalized and accurate treatment according to the risk assessment; iii) facilitating to develop early diagnosis and operation plan for metastatic tumor. The latest researches show that somatic mutations of RET, NF1, VHL, MAX, HIF2A, HRAS can be detected in more than one third of PCC and PGL patients. Therefore, somatic mutation detection of susceptibility genes is also recommended for early diagnosis and preoperative assessment of PCC and PGL patients. However, relative to the detection of germline mutations, somatic mutation detection still relies on tumor tissue samples, which greatly restricts the genetic testing for preoperative evaluation and early diagnosis. In this aspect, the development of liquid biopsy technique is of great clinical significance for the early diagnosis and preoperative evaluation of PCCs and PGLs. In the existing technologies, the related research is a technical blank, which needs to be solved urgently.

Exosomes are extracellular vesicles (with diameter of 50-150 nm) found in the body fluids, which are formed through process of cell endocytosis-fusion-exocytosis. Exosomes in the tumor microenvironment may play a key role in facilitating cell-cell communication. The biological information carried by exosome is expected to be used in the early diagnosis of tumors by liquid biopsy detection. However, whether exosomes from PCC and PGL patients carry genetic information that reflects the parental tumor cells remains unknown.

SUMMARY OF THE INVENTION

To solve the above problems, the present invention disclosed a double-stranded DNA biomarker derived from exosomes for the early diagnosis and preoperative assessment of pheochromocytoma and paraganglioma. The biomarker is a genome double-stranded DNA fragment specifically derived from exosomes in peripheral blood serum of pheochromocytoma and paraganglioma patients. Through sequencing identification, iPLEX mutation analysis, next-generation sequencing, and bioinformatics alignment analysis, it is found that this double-stranded DNA could represent variations of RET, VHL, and HIF2A with high frequency of somatic cell mutation and metastatic phenotype-related SDHB, which are susceptibility genes of PCCs and PGLs. The exosome double-stranded DNA contains 97% of the same chromosomal point mutation information as the tumor cells from which the DNA originated.

In the present technical solution, the biomaker of exosome double-stranded DNA is derived from cell lines associated with PCCs and PGLs, the serum of nude mice implanted with mutated xenografts, and the serum of PCC and PGL patients. The biomaker of exosome double-stranded DNA is a double-stranded DNA fragment.

In the above technical solution, a preferred extraction process of the double-stranded DNA fragment includes, treatment of exosome samples with DNase I to digest the external DNA with preferred treatment condition of 10-25 min at room temperature; digestion of the external RNA with RNase A; chelation with EDTA; digestion with proteinase K at 50-60° C. for 5-20 min in accordance with the volume ratio of exsome sample and proteinase K of 1:20-100 to digest the DNase I, RNase A and other external proteins. A preferred volume ratio of the exosome sample and proteinase K is 1:20-40, a preferred digestion temperature for proteinase K is 56° C., and a preferred digestion time is 10 min.

In the above technical solution, the specific optimization program for the isolation process of exosomes includes isolation of exosomes from the conditioned medium collected from PC12 cells, the serum of nude mice implanted with mutated xenografts, or PCC or PGL patient serum, respectively.

The protocol of exosome extraction from cell lines associated with PCCs and PGLs includes: taking culture medium of cell lines associated with PCCs and PGLs, which is subjected to centrifugation at 3,000-5,000 rpm for 10-20 min at 4° C. to remove cellular debris and dead cells; then collecting supernatants for differential centrifugation at 100000-150000 g for 1-5 h; washing the collected exosome pellets and subjecting to centrifugation at 100000-150000 g for 1-2 h; collecting pellets for re-suspending.

In detail, the protocol of exosome extraction from PCC or PGL patient serum includes: centrifuging the peripheral blood samples at 3,000-5,000 rpm for 5-20 min to collect the serum at 4° C.; centrifuging the collected serum again at 3,000-5,000 rpm for 5-20 min; proceeding the supernatant solution to high-speed centrifugation at 100000 g-120000 g for 1-5 h, washing and re-suspending the pellets to obtain the exosome.

In general, the pellet washing in the extraction method of exosomes is usually carried out with a neutral buffer solution, for example, washing 1-3 times with PBS solution.

Another aspect of this invention is that applications of the biomarkers disclosed in the present invention in early diagnosis and preoperative evaluation of PCCs and PGLs are disclosed.

Another aspect of this invention is that applications of the biomarkers disclosed in the present invention in the detection of variations of RET, VHL, and HIF2A (with high frequency of somatic cell mutation) and SDHB (metastatic phenotype-related), are disclosed. These four genes are susceptibility genes of PCCs and PGLs.

Another aspect of this invention is to provide a susceptibility gene detection kit for PCCs and PGLs, which includes reagents used to detect the biomarkers disclosed in the present invention.

For the susceptibility gene detection kit for PCCs and PGLs, the biomarker detection reagents include DNase I, RNase A, EDTA and proteinase K.

For the susceptibility gene detection kit for PCCs and PGLs, the use of the kit includes the following steps: treating the exosome samples with DNase I at room temperature to digest the external DNA; digesting the external RNA with RNase A; chelation with EDTA; digesting DNase I, RNase A and other external proteins with proteinase K at 50-60° C. for 5-20 min in accordance with the volume ratio of exosome sample and proteinase K of 1:20-100. The dosages of DNase I and RNase A are not specified, because these dosages are common knowledge for those skilled in the art in this field. In general, those skilled in the art in this field can adjust the dosage and action time of DNase I and RNase A for the purpose of "digesting external DNA" and "digesting external RNA".

Beneficial Effects of the Invention

1. The present invention is the first to reveal and provide the evidence for the main existence of double-stranded DNA fragments in the serum exosomes of PCCs and PGLs.
2. The double-stranded DNA from PCC and PGL exosomes in the present invention could be used to identify mutations that exist in tumor cells, and be used as a noninvasive molecular markers for clinical diagnosis and preoperative evaluation of PCCs and PGLs.
3. According to the analysis of measuring data in the invention implementation, RET, HIF2A, VHL, and SDHB mutations detected in the exosome DNA, by the method described in the present invention, are completely consistent with the tumor somatic mutations of PCCs and PGLs. Exosome DNA is highly consistent with the corresponding tumor gene DNA. Therefore, the detection technology provided by the present invention can offer an effective method for preoperative screening of pheochromocyte somatic mutation.

BRIEF DESCRIPTIONS OF THE DRAWINGS

FIG. 7 Whole-genome sequencing results of serum-derived exosome DNA and the genome DNA of corresponding primary tumor from 3 patients (a-c); wherein, in the whole-genome sequencing analysis of exo-DNA III, FIG. 7 shows the distribution of all SNP on each chromosome. The inner and outer tracks indicate the SNP counts for the exosomes and paired PCC or PGL samples, respectively.

DETAILED DESCRIPTION

Example 1

1 Patients and Tissue Samples Collection 15 clinical cases of sporadic PCC and PGL and tumor samples were collected for gene testing. Among them, three of the tumors did not have germline or somatic mutations in the 12 known susceptibility genes, the other 12 tumors had RET, VHL, HIF2A, and SDHB somatic mutations. There was no adjuvant radiotherapy or chemotherapy before tumor resection. Peripheral blood (10 ml) was collected from each patient. The blood samples were subjected to centrifugation at 3,000 g for 10 min at 4° C., to isolate serum for the extraction and analysis of exosome and DNA.

2 Cell Culture

During PC12 cell culture, to avoid contamination from the exosomes in serum, the fetal bovine serum (FBS) and horse serum (HS) was subjected to ultracentrifugation for 11 h at 100,000 g. The supernatant was taken. PC12 cells were cultured in basic medium RPMI 1640 (Gibco) with 10% HS (exosome-depleted) and 5% FBS (exosome-depleted), with medium changes every 48 h. We passaged cells when the total number of cells accounted for 70-80% of the bottom area of the culture bottle, and collected the conditioned medium (250 ml), which was stored at −80° C.

3 Cell Transfection

1) PC12 cells were cultured up to 8th passage. Two hours after changing the medium with penicillin- and streptomycin-free medium, the transfection reagent mixed with plasmid was added in Opti-MEM. After washing with phosphate-buffered saline (PBS), the complete medium was changed. The culture medium 48 h after transfection (150 ml) was collected and stored at −80° C.

2) PC12 cells were seeded into a 96-well plate to culture. After 24 h, adenovirus was used to introduce mutation sites. After 72 h, fluorescence microscopy was used to detect the viral infection efficiency. 10 μL mutant plasmid of RET, VHL, HIF2A and SDHB was taken, respectively. 30 mol/L adenovirus with different mutations and reagents were used to infect PC12 cells. Stably infected cells were screened by neomycin resistance genes for tumor transplantation in animals.

4 Xenotransplantation In Vivo Experiment

30 BALB/c nude mice (4-6 weeks old) were used for the animal xenograft experiments. 0.2 mL PBS cell solution with stably infected PC12 cells (RET, VHL, HIF2A, and SDHB mutations) was prepared, and the cell density was $7 \times 10^7$. The cell solution was subcutaneously injected in the back flank skin of each mouse. After 35 d, the tumor in the mice body reached the maximum size. Serum was isolated from mouse venous blood and used for isolation of genome DNA for mutation detection.

Example 2

1 Isolation and Characterization of Exosomes from Cells and Serum

Exosomes were isolated from the medium collected from PC12 cells, the serum of nude mice implanted with mutated xenografts, and PCC and PGL patient serum, respectively.

1) PC12 cells in a logarithmic growth period were chose, and its medium was replaced with medium containing 10% HS and 5% FBS that had been depleted of exosomes. Then, the conditioned medium was subjected to centrifugation at 3,000 rpm for 10 min at 4° C. to remove cellular debris and dead cells. The supernatants were subjected to differential centrifugation at 100,000 g for 2.5 h. The exosome pellets were washed with 1×PBS one time and subjected to centrifugation at 100,000 g for 70 min. The final exosome pellets were re-suspended in 1×PBS.

2) To isolate exosomes from the peripheral blood, samples were subjected to centrifugation at 3,000 rpm for 15 min at 4° C. to separate the serum. The collected serum was centrifuged at 3,000 rpm for 10 min, then the supernatant was experienced to centrifugation, washing and re-suspending, as described in step 1).

Figure 1:
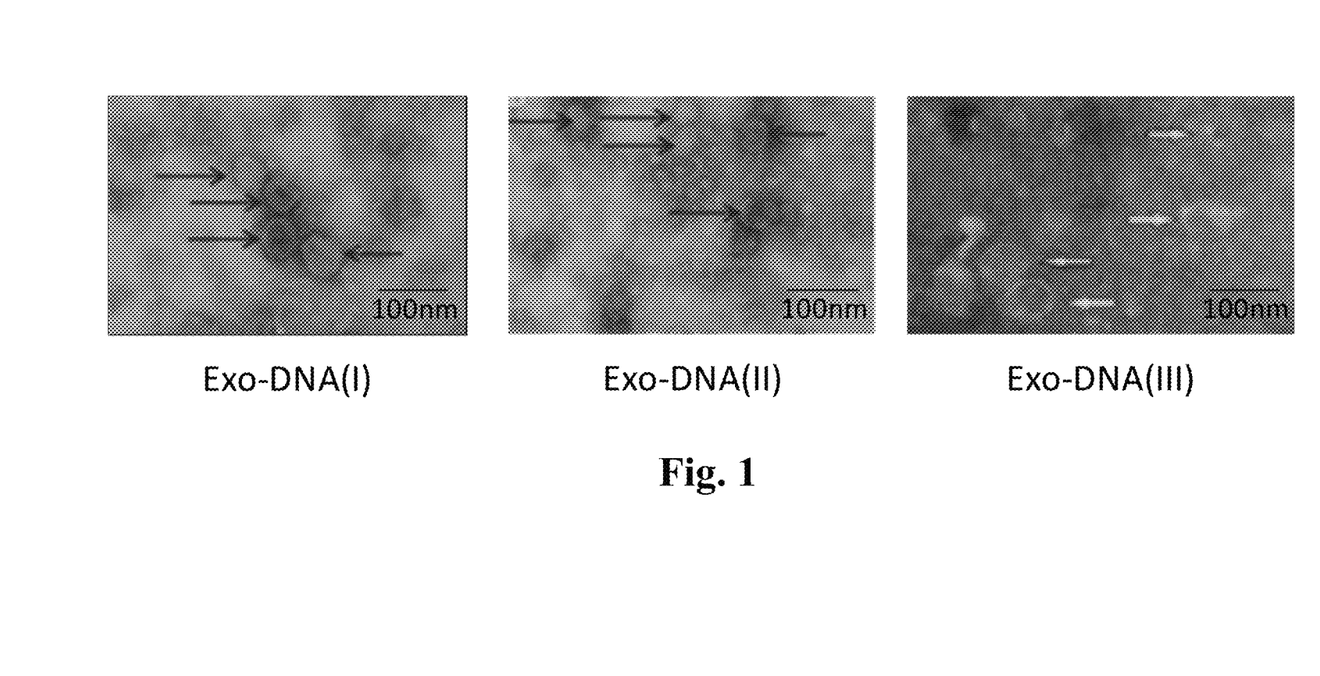
FIG. 1 The SEM pictures of exosomes from the PC12 cell line, serum samples from nude mice with mutated xenografts, and PCC and PGL patients were determined by electron microscopy; wherein, the exo-DNA I, exo-DNA II, and exo-DNA III represent exosome DNA separated from PC12 cell line, serum of nude mice with mutated xenografts, and serum of PCC and PGL patients, respectively.
Figure 2:
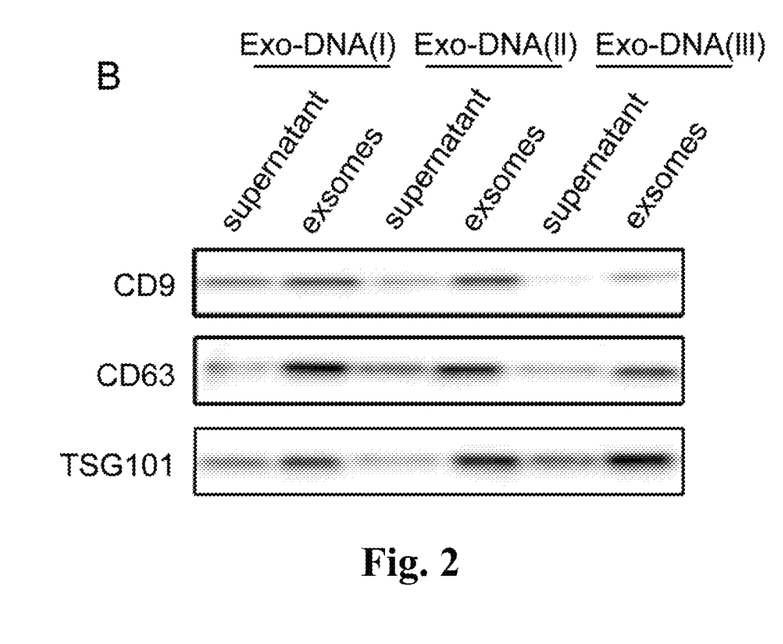
FIG. 2 The results of exosomes from the PC12 cell line, serum samples from nude mice with mutated xenografts, and PCC and PGL patients, for the expression of exosome-specific marker TSG101, CD9 and CD63, by western blotting assay.

3) Exosomes (5 μL) were fixed with 4% paraformaldehyde (5 μL) at room temperature for 30 min and stored at −4° C. overnight. The samples were mixed by ultrasound equipment before adding them to copper wire mesh where they settled for 30 min, then were stained with phosphotungstic acid for 5 min. The samples were observed with a transmission electron microscope and recorded morphology of exosomes. FIG. 1 is the electron microscope characterization, and FIG. 2 is the expression of exosome markers (TSG101, CD9 and CD63). The results confirm the existence of exosomes and their characteristic properties in PC12 cells and serum samples.

2 Western Blotting Analysis

According to standard protocols, the total protein was extracted and quantified from the exosome samples (30 μL). Total protein (30 μg) was subjected to western blotting and then detected exosome markers (CD9, CD63, and TSG101).

3 Extraction and Identification of Exosomal DNA

1) Before extracting exosomal DNA, to reduce the contamination of external DNA and RNA, the samples was treated with DNase I (10 μL) and RNase A (4 μL) at room temperature for 15 min to digest the external DNA and RNA, respectively. Then, the samples were treated with 140 mol EDTA to chelate and were treated with proteinase K (10 μL) at 56° C. for 10 min to digest the DNase I, RNase A, and other external proteins. The extracted DNA was quantified with a NanoDrop™ 2000, and was assessed its quality by agarose gel electrophoresis (1% agar, U=100 v, I=50 mA).

Figure 3:
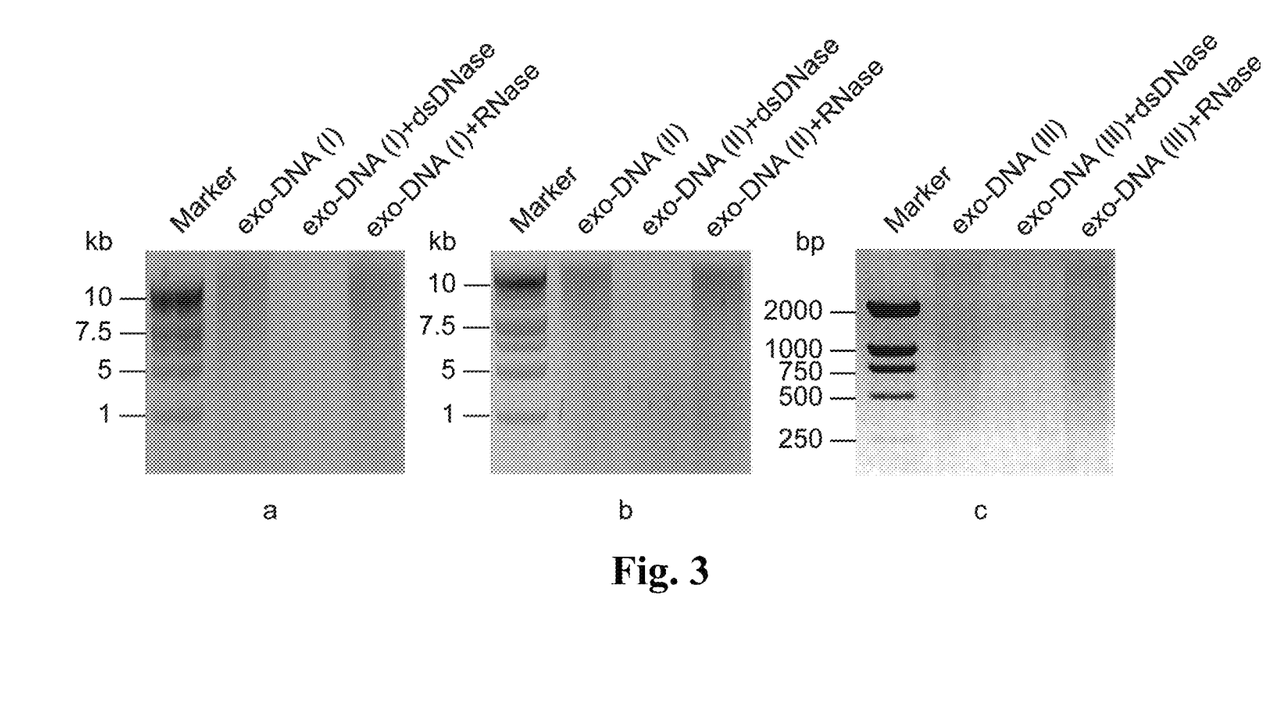
FIG. 3 Detection results of exosome double-stranded DNA from a) PC12 cell line, b) serum of nude mice with mutated xenografts, and c) serum of PCC and PGL patients, respectively.

2) dsDNase (1 μL) was respectively added to the DNA samples (0.5 μg) from exosomes and PC12 cells, at 37° C. for 2 min to digest the double-stranded DNA in the two samples. The samples were subjected to agarose gel electrophoresis for qualitative and relatively quantitative analysis of the total DNA. The results indicate that, as shown in FIG. 3, most of the DNA in exosomes from the three sources is digested by dsDNase, which is not digested after RNase treatment.

4 iPLEX Mutation Analysis

Figure 4:
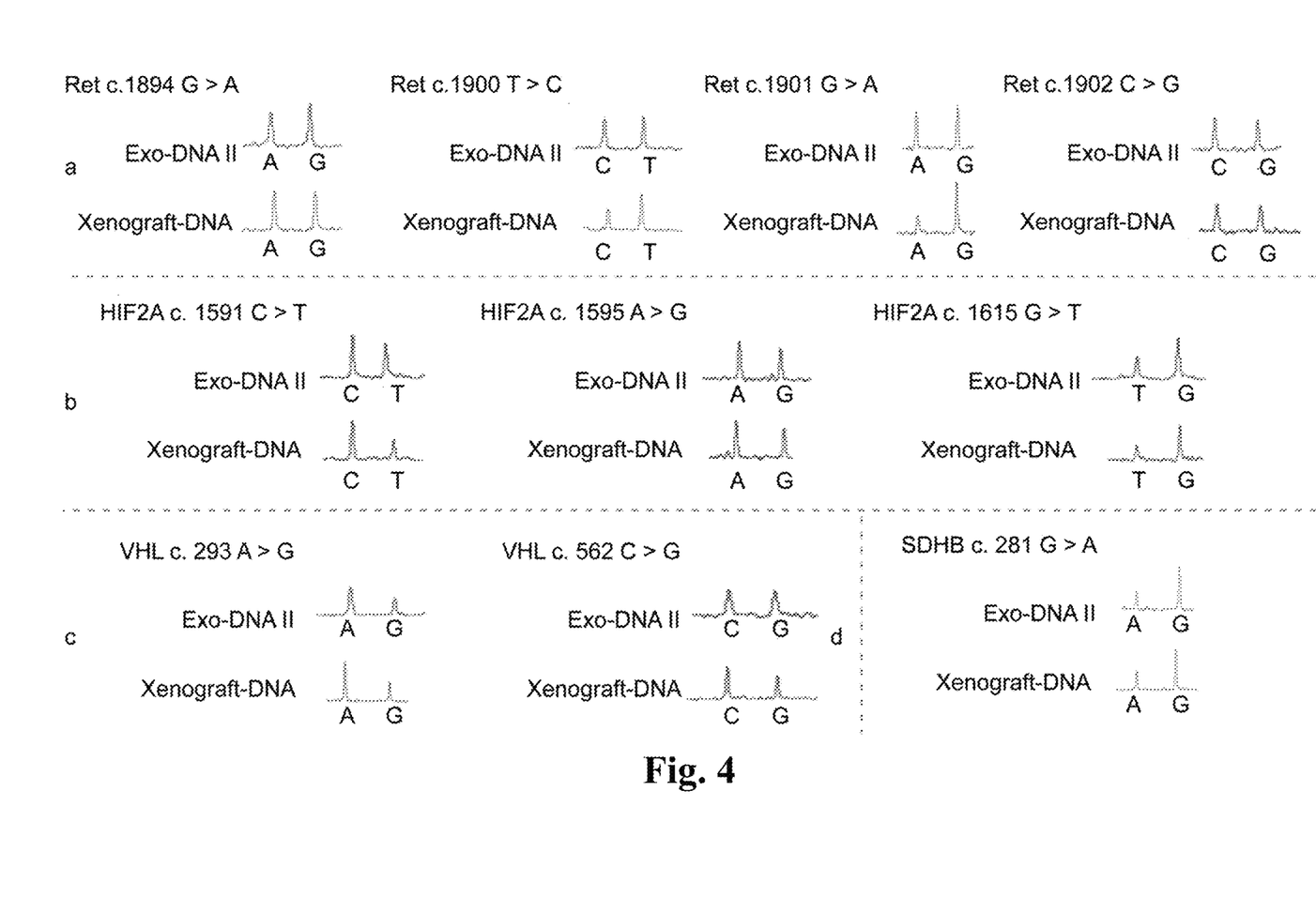
FIG. 4 iPLEX mutation analysis of genomic DNA revealed that the exosome DNA from PC12 cells which are transfected with plasmids expressing RET, HIF2A, VHL, and SDHB mutations, contains mutation pattern consistent with the transfected cells.

Genomic DNA was isolated and purified using a genomic DNA separation kit (Qiagen). DNA mutation was detected by Mass ARRAY iPLEX system, a mass spectrometry-based method. Specific primers were designed using Sequenom Online Tools (Assay Design Suite, AgenaCx). RET, HIF2A, VHL and SDHB mutations are the most common mutations in sporadic PCCs and PGLs. The results indicate that identical mutations are detected in transfected PC12 cells and in exosome DNA extracted from the culture medium (FIG. 4), which prove that the detection of tumor susceptibility gene mutation by the circulating exosome DNA is feasible.

5 Next-Generation Sequencing (NGS)

1) Whole-genome sequencing of the DNA (30 μL) extracted from 3 PCC/PGL patient tumors and their serum exosomes were performed. The genomic DNA from PC12 cells and their exosomes were also assayed by NGS according to a standard operating procedure.

Figure 5:
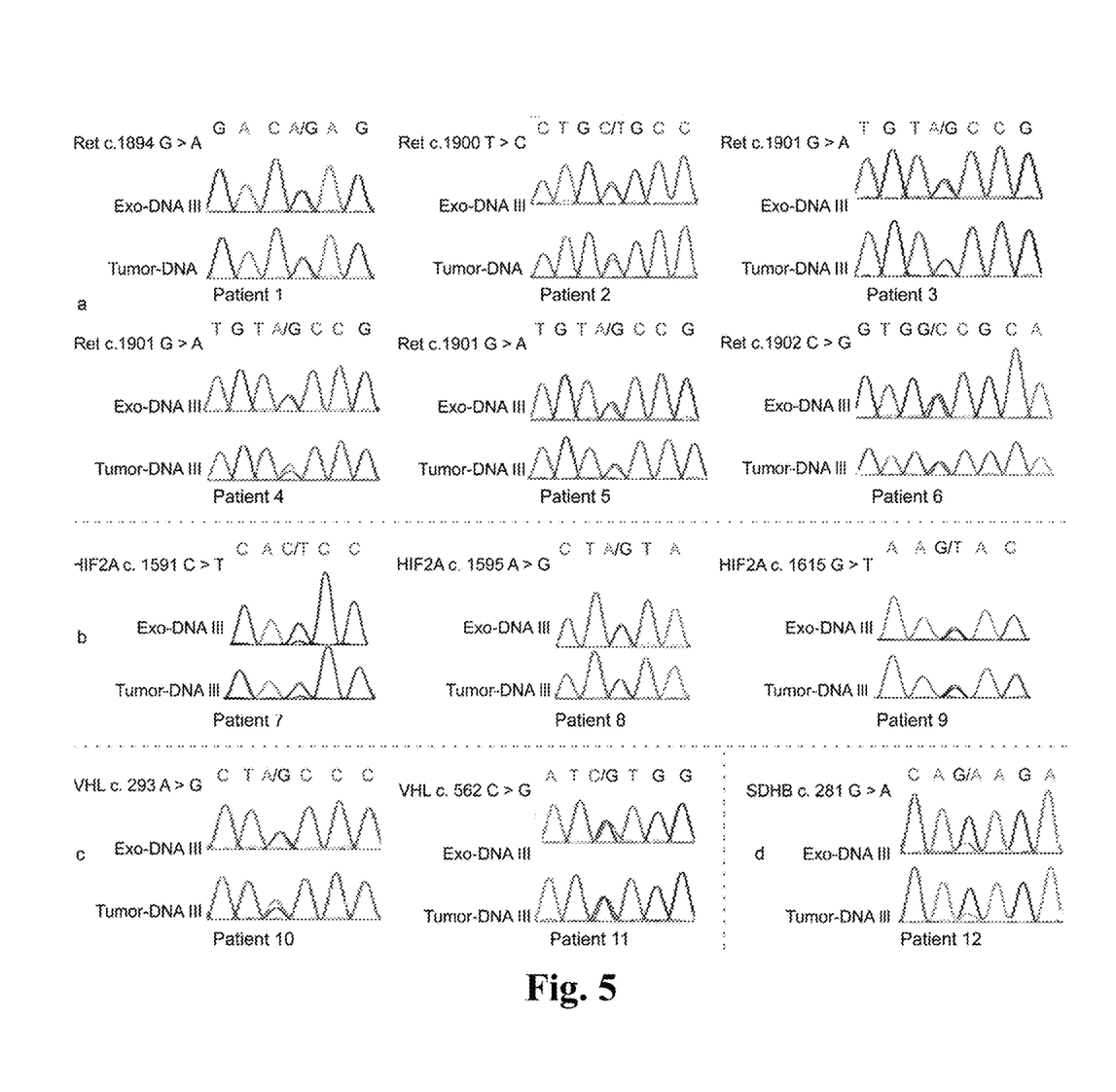
FIG. 5 Sanger sequencing of serum exosome-derived DNA could detect somatic mutations (RET, HIF2A, VHL, and SDHB mutations) in PCC and PCL patients.

2) The mutated RET, VHL, HIF2A and SDHB fragments from 12 PCC and PGL patients (identified with susceptibility gene somatic cell mutation by genetic diagnosis) were amplified. PCR amplification was performed on DNA isolated from tumor and genomic DNA derived from serum exosomes of the patients. Detection of Sanger sequencing indicated that the patient's serum sample had all the same genetic mutations as the parental tumor tissue (FIG. 5). It's found that the RET, HIF2A, VHL, and SDHB mutations in serum exosomal DNA were definitively consistent with the somatic tumor mutations in patients with PCC or PGL. It is proved that the detection of exosomal DNA mutation makes it possible for further somatic cell mutation detection in patients with negative germline mutation detection. Therefore, it provides a reliable evidence for preoperative evaluation of these PCC and PGL patients (about ⅓).

6. Dynamic Light Scattering (DLS) Analysis of Exosomes

Exosomal protein was eliminated with proteinase K according to the manufacturer's instructions (DNA isolation kit, Qiagen). The sizes of the exosomes were measured with a Zetasizer (Malvern Panalytical). Exosomes (diluted 1:200 in PBS) were analyzed with an equilibration time of 70 s at a constant temperature of 25° C. A laser beam (549 nm) was applied to the exosome suspension and the scattered light was detected by an avalanche photodiode detector at 173° with noninvasive back scattering optics. The average of the three measurements was used to determine the sizes of the exosomes.

7. Bioinformatics Alignment Analysis

1) The sequencing depth and distribution of mutations were illustrated with Circos software (v 0.67). The alignment result file (BAM) was used to calculate the depth of the whole-genome sequencing at each locus. The mutation analysis results file (VCF) was simultaneously applied to calculate the mutation positions in the whole genome.

Figure 6:
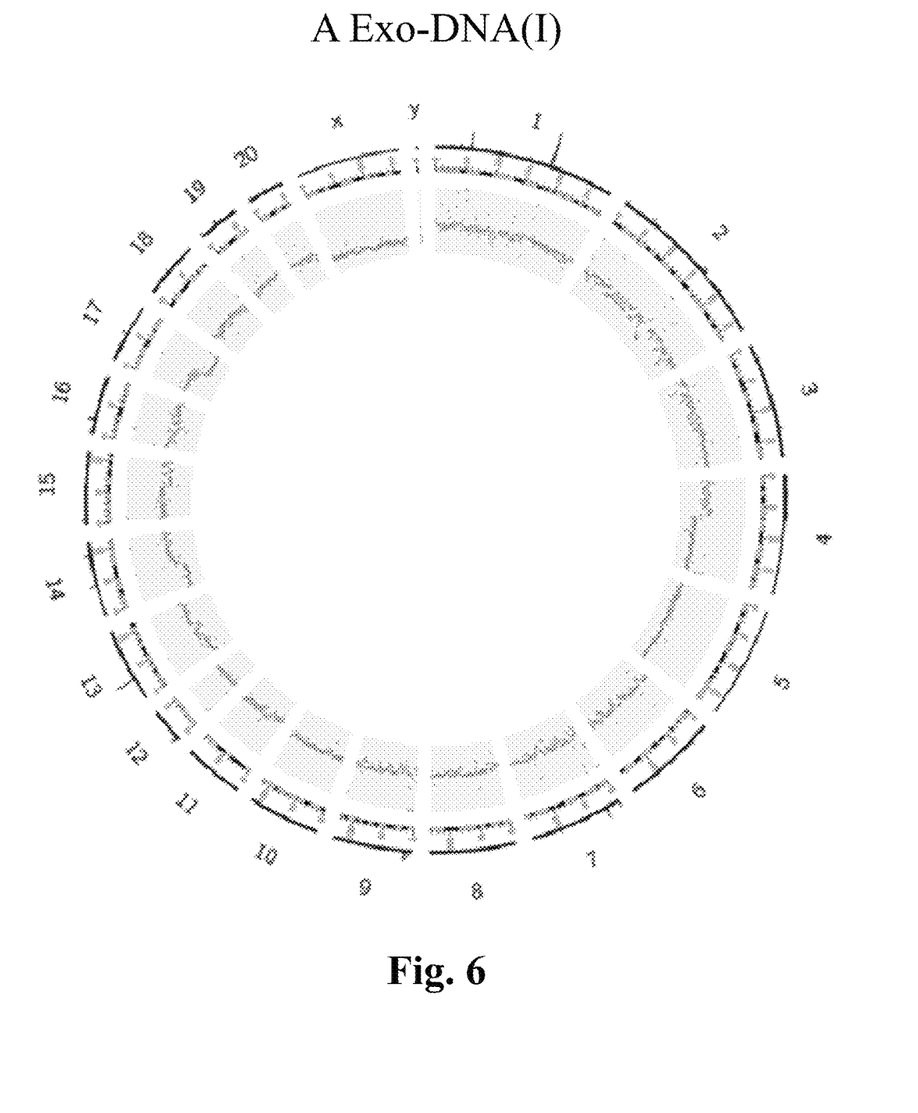
FIG. 6 According to the whole-genome sequencing of PC12 cell line and culture medium exosomes (b), the mutations in exo-DNA I are displayed in a chromosome map (a); wherein, the bar on the outer circle indicates the average depth of the sequence and the dots in the inner ring represent the number of mutations.

2) To determine if the double-stranded DNA from the circulating exosomes reflects the mutational status of their parental tumor cells, the exosomal DNA from the PC12 supernatants (exo-DNA I) was compared with PC12 genomic DNA. The whole-genome sequencing results demonstrated that exo-DNA I covered 97.7% of the single nucleotide polymorphisms (SNPs) of the parent PC12 cells (FIG. 6), which proves the detection of tumor susceptibility gene mutation by circulating exosome DNA can be used to detect somatic cell mutation, providing reliable genetic testing data for preoperative evaluation.

Figure 7:
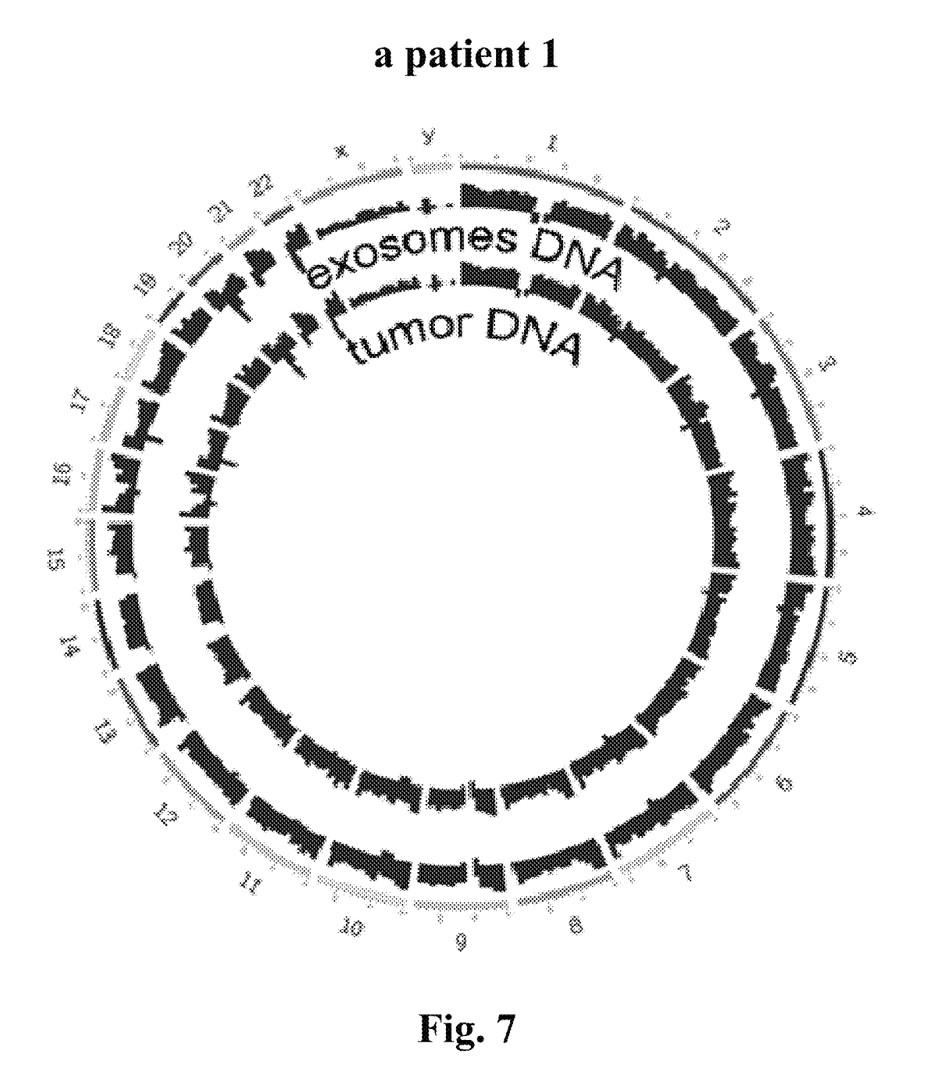
Figure 8:
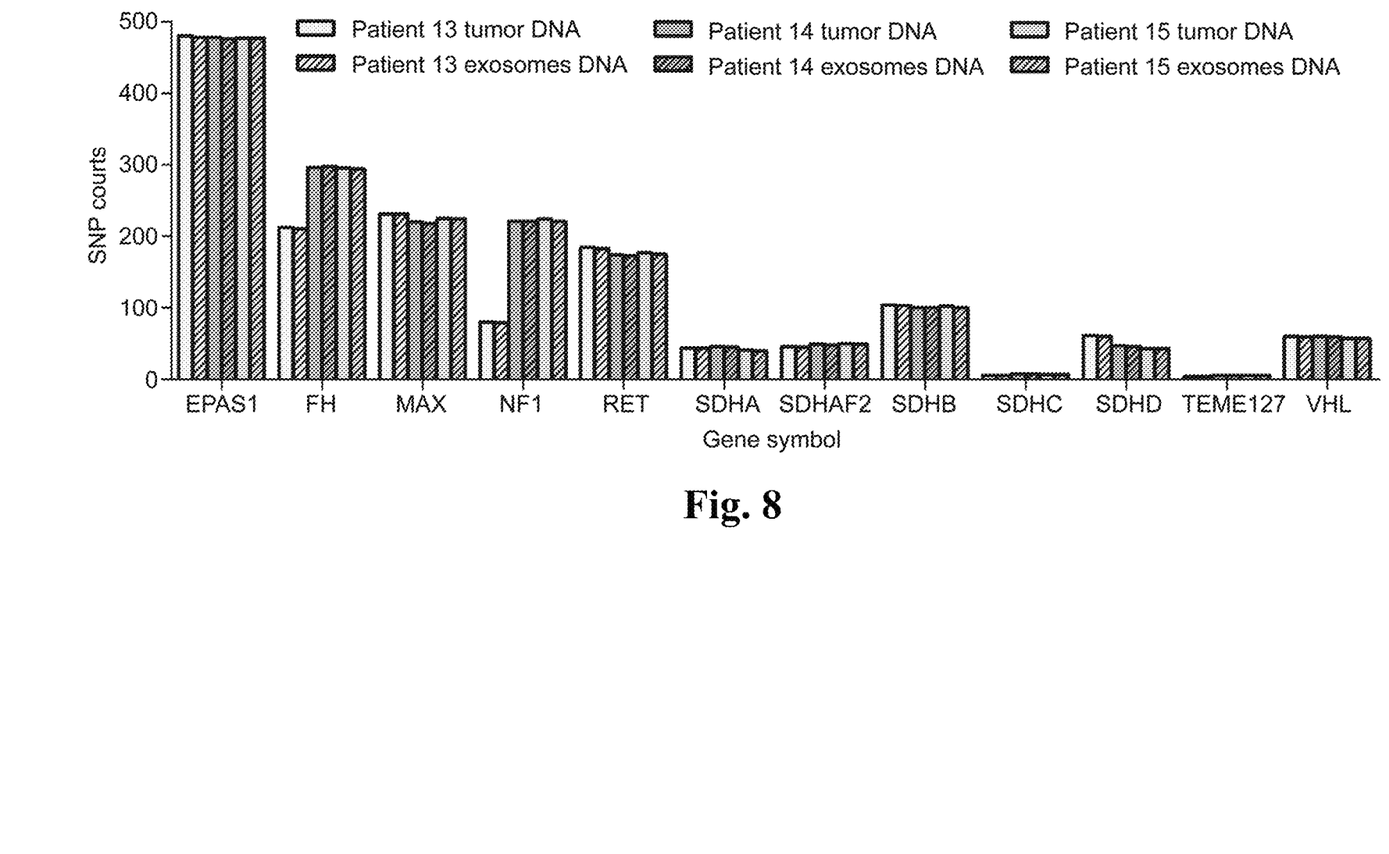
FIG. 8 All common SNP counts of the 12 susceptibility genes for PCC and PGL showed with their relative proportion.

3) The present example compared the genomic DNA in the serum exosomes and paired tumor tissues of 3 PCC/PGL patients. High-throughput whole-genome sequencing was also performed to further characterize the DNA SNP locus from the serum exosomes of the 3 patients. The results revealed that the entire genome is covered by the exosomal DNA in an unbiased manner (FIG. 7). In addition, compared to genomic DNA, no specific enrichments or depletions were observed in the exosomal DNA fragments. By detecting 12 driver susceptibility gene SNP, the concordance rates of the mutations in the exosomal and tumor tissue DNA were as high as 97.6%-100% (FIG. 8). The results demonstrate a high degree of consistency between serum exosomal DNA and paired tumor genomic DNA of patients with PCC or PGL.

For those skilled in the art, without departing from the scope of technical solutions of the present disclosure, many possible variations and modifications can be made to the technical solutions of the present disclosure by using the technical contents disclosed above, or to modify the equivalent embodiments with equivalent changes. Therefore, any simple changes, equivalent changes and modifications of the above embodiments made according to the technical essence of the present disclosure without departing from the technical solutions of the present disclosure shall belong to the scope of protection of the present disclosure.

The invention claimed is:

1. A method for detecting in a patient the presence of a exosomal biomarker, comprising:
   (a) drawing a peripheral blood sample from a patient having pheochromocytoma or paraganglioma;
   (b) centrifuging the sample at 3,000-5,000 rpm to collect serum at 4° C.;
   (c) centrifuging the collected serum again at 3,000-5,000 rpm to obtain a supernatant;
   (d) centrifuging the supernatant at 100000 g-120000 g, washing and re-suspending the resulting precipitate to obtain an exosome sample;
   (e) treating the exosome sample with DNase I;
   (f) digesting the treated exosome sample with RNase A to digest external RNA;
   (g) chelating the RNase A-digested exosome sample with EDTA;
   (h) digesting the exosome sample from step (g) with proteinase K at 50-60° C. for 5-20 min in accordance with the volume ratio of the exosome sample and proteinase K of 1:20-100 to digest the DNase I, RNase A and other external proteins to obtain a nucleic acid sample; and
   (i) identifying the nucleic acid sample for the presence or absence of a biomarker, wherein the biomarker contains at least one double-stranded DNA fragment having a variation of SDHB and the variation is the c.281 G>A mutation in the SDHB coding sequence.

2. The method according to claim 1, wherein a duration of centrifuging at 3,000-5,000 rpm is 5-20 min.

3. The method according to claim 1, wherein a duration of centrifuging the supernatant is for 1-5 h.

4. The method according to claim 1, wherein the treating the exosome samples with DNase I is carried out for 10-25 min at room temperature to digest external DNA.

5. The method according to claim 1, wherein the digestion temperature for proteinase K is 56° C. and the digestion time is 10 min.

6. The method according to claim 1, wherein the volume ratio of the exosome sample and the proteinase K is 1:20-40.

7. The method according to claim 1, wherein the step (i) of identifying the presence or absence of a biomarker comprises detecting DNA mutation using a mass spectrometry.

* * * * *